United States Patent [19]
Rittinger et al.

[11] Patent Number: 5,972,064
[45] Date of Patent: Oct. 26, 1999

[54] USE OF LOW-VOLATILITY PYRAZOLE DERIVATIVES HAVING HYDROPHILIC GROUPS AS NITRIFICATION INHIBITORS

[75] Inventors: Stefan Rittinger; Norbert Rieber, both of Mannheim; Randall Evan Gold, Limburgerhof; Jürgen Dressel, Neuhofen, all of Germany

[73] Assignee: BASF Aktiengesellschaft, Ludwigshafen, Germany

[21] Appl. No.: 08/875,755

[22] PCT Filed: Jan. 26, 1996

[86] PCT No.: PCT/EP96/00319

§ 371 Date: Aug. 6, 1997

§ 102(e) Date: Aug. 6, 1997

[87] PCT Pub. No.: WO96/24566

PCT Pub. Date: Aug. 15, 1996

[30] Foreign Application Priority Data

Feb. 6, 1995 [DE] Germany ............. 195 03 827

[51] Int. Cl.⁶ .......... C07C 11/08; C07D 231/16; C07D 231/20; C07D 231/22
[52] U.S. Cl. .......... 71/27; 548/377.1; 548/376.1; 548/372.1; 548/372.5
[58] Field of Search .............. 548/377.1, 376.1, 548/372.1, 377.5; 71/27

[56] References Cited

U.S. PATENT DOCUMENTS

| 3,303,200 | 2/1967 | Wolf et al. ............... 260/310 |
| 3,635,690 | 1/1972 | Griffith ................... 71/1 |
| 4,084,955 | 4/1978 | Kornis et al. .............. 71/92 |

FOREIGN PATENT DOCUMENTS

| 2406616 | 5/1979 | France . |
| 131063 | 5/1978 | Germany . |
| 133088 | 12/1978 | Germany . |
| 2745833 | 4/1979 | Germany . |
| 7711661 | 4/1979 | Netherlands . |

OTHER PUBLICATIONS

DM. Huber et al, "New Tools for Food Production", BioScience vol. 27, No. 8, pp. 523–529, Aug. 1977.

*Primary Examiner*—Johann Richter
*Assistant Examiner*—Dominic Keating
*Attorney, Agent, or Firm*—Oblon, Spivak, McClelland, Maier & Neustadt, P.C.

[57] ABSTRACT

The present invention provides pyrazole compounds which are useful as nitrification inhibitors.

9 Claims, No Drawings

USE OF LOW-VOLATILITY PYRAZOLE DERIVATIVES HAVING HYDROPHILIC GROUPS AS NITRIFICATION INHIBITORS

BACKGROUND OF THE INVENTION

1. Field of the Invention

The present invention relates to the use of pyrazole derivatives of the formula I

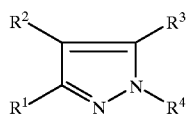

or their acid addition salts as nitrification inhibitors, where the radicals $R^1$, $R^2$, $R^3$ and $R^4$ have the following meanings:

$R^1$, $R^2$ and $R^3$ are halogen, nitro, hydrogen, $C_1$- to $C_{20}$-alkyl, $C_3$- to $C_8$-cycloalkyl, $C_5$- to $C_{20}$-aryl or alkylaryl, it being possible for these 4 radicals to be monosubstituted or disubstituted by halogen and/or hydroxyl $R^4$ is either a) a radical $R^{4a}$ having the formula II

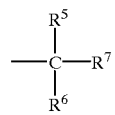

where $R^5$ and $R^6$ are hydrogen, $C_1$- to $C_{20}$-alkyl which can be monosubstituted or disubstituted by halogen and/or hydroxyl, a carboxyl group, a carboxymethyl group or a functional derivative of the two last-mentioned groups, and $R^7$ is a carboxyl radical or a carboxy-($C_1$- to $C_3$-alkyl) radical or a functional derivative of these groups or b) a radical $R^{4b}$ having the formula III

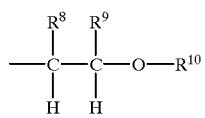

where $R^8$ and $R^9$ are hydrogen, $C_1$- to $C_{20}$-alkyl, $C_3$- to $C_8$-cycloalkyl, $C_5$- to $C_{20}$-aryl or alkylaryl, it being possible for these 4 radicals to be monosubstituted or disubstituted by halogen and $R^{10}$ is hydrogen or a poly-($C_2$- to $C_4$-alkylene oxide) radical whose terminal hydroxyl group can be etherified by an aliphatic $C_1$- to $C_{10}$-alkohol or esterified by a $C_1$- to $C_{10}$-carboxylic acid.

The invention furthermore relates to novel pyrazole derivatives which are suitable for this intended use, processes for their preparation and fertilizer mixtures which contain such pyrazole. derivatives.

2. Description of the Background

In order to make available to plants the nitrogen needed by them, they are fertilized, as is known, with ammonium compounds. Ammonium compounds, however, are microbially converted to nitrate in the soil in a relatively short time (nitrification).

Because nitrate is leached from the soil more easily than ammonium and the leached portion is no longer available for plant nutrition, however, rapid nitrification is undesirable. In order that the fertilizer is utilized better, it was therefore proposed to add nitrification inhibitors to the soil.

EP-A 474 037 discloses 3-methylpyrazole derivatives in which one nitrogen atom of the pyrazole ring carries a methyl, cycloalkyl, aryl or aralkyl radical. It is proposed to use these compounds as intermediates for the preparation of pharmaceutical products or crop protection agents.

U.S. Pat. No. 3,635,690 discloses the employment of various pyrazole derivatives for the inhibition of nitrification. In the pyrazole derivatives proposed, the nitrogen atoms in the pyrazole ring do not carry any substituents or one of the nitrogen atoms carries a saturated or unsaturated $C_1$- to $C_3$-hydrocarbon radical. One or more carbon atoms in the pyrazole ring can be substituted by hydrocarbon radicals which may carry halogens as substituents. Examples of these are 3-methylpyrazoles such as 4-chloro-3-methylpyrazole.

U.S. Pat. No. 4,969,946 also describes the use of pyrazole derivatives as nitrification inhibitors. In these derivatives, the nitrogen atoms in the pyrazole ring are unsubstituted, and several of the ring carbon atoms are substituted by halogen or methyl.

DE-A 3 704 359 relates to compositions which inhibit nitrification. As active compound, they contain pyrazole derivatives which, on one nitrogen atom of the pyrazole ring, carry a radical of the formula

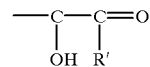

where R' is a substituted or unsubstituted organic radical or a hydroxyl radical.

Further nitrification inhibitors are disclosed in EP-A 0 160 804. They are pyrazole derivatives in which a nitrogen atom in the pyrazole ring carries a substituted oxycarbonyl, sulfinyl or sulfonyl radical.

DE-A 4 018 395 mentions derivatives of 1-cyano-3-methylpyrazole and its acid addition products or coordination compounds as nitrification inhibitors.

SU-A 1 470 737 discloses N-hydroxymethyl derivatives of pyrazole.

These active compounds are still not entirely satisfactory as nitrification inhibitors as they have one or more of the following disadvantages:

excessively low activity based on the application rate;

excessively low stability against hydrolysis, whereby the duration of action in the soil and the stability on storage is reduced. This relates especially to pyrazole derivatives such as N-glyoxylpyrazoles and N-hydroxymethylpyrazoles, and mineral acid salts of pyrazoles;

excessively high toxicity or ecotoxicity;

only accessible by complicated preparation processes (eg. N-hydroxypyrazoles);

excessively low absorption of the compounds in the soil, whereby they are rapidly leached;

excessively high volatility. This results in the compounds being easily given off from the soil into the atmosphere unless the compounds are introduced into the soil using technically complicated processes (eg. by probe).

SUMMARY OF THE INVENTION

It is an object of the present invention to find and make available substances which act as nitrification inhibitors and which do not have the disadvantages mentioned.

The object specifically applies to the discovery of known compounds having the desired properties, and the synthesis of novel compounds having properties of this type.

We have now found that this object is achieved by the pyrazole derivatives of the formula I, which are suitable as nitrification inhibitors. Furthermore, the compounds of the formula Ia according to the invention

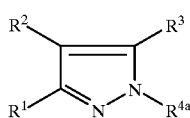

where $R^1$ and $R^3$ have the meanings indicated for the formula I, $R^2$ is halogen and $R^4$ is a radical having the formula II, the substituents $R^5$, $R^6$ and $R^7$ having the meanings indicated for the formula I, and the formula Ib

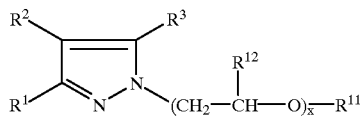

where $R^1$ and $R^3$ have the meanings indicated for the formula I, $R^2$ is halogen $R^{11}$ is hydrogen, $C_1$- to $C_{20}$-alkyl, $C_3$- to $C_8$-cycloalkyl or $C_1$- to $C_{10}$-acyl $R^{12}$ is hydrogen or methyl x is 1 to 10 and the acid addition salts of the compounds of the formulae Ia and Ib were provided.

DETAILED DESCRIPTION OF THE INVENTION

Compounds suitable for use as nitrification inhibitors are particularly those where the substituents $R^1$, $R^2$ and $R^3$ are $C_1$- to $C_5$-alkyl or halogen. Suitable alkyl radicals are especially methyl and ethyl and suitable halogen radicals are Br, Cl and F. The pyrazole derivatives of the formula I particularly preferably contain units which are derived from 4-methylpyrazole, 4-chloropyrazole, 3-methylpyrazole, 5-methylpyrazole, 4-chloro-3-methylpyrazole, 4-chloro-5-methylpyrazole and 3,4-dimethylpyrazole.

Suitable $R^4$ radicals are either a) $R^{4a}$ radicals having the formula II

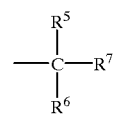

where $R^5$ and $R^6$ are hydrogen, $C_1$- to $C_{20}$-alkyl which can be monosubstituted or disubstituted by halogen and/or hydroxyl, a carboxyl group, a carboxymethyl group or a functional derivative of the two last-mentioned groups, and $R^7$ is a carboxyl radical or a carboxy-($C_1$- to $C_3$-alkyl) radical or a functional derivative of these radicals or b) R4b radicals having the formula III

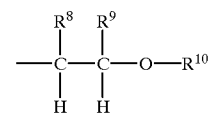

where $R^8$ and $R^9$ are $C_1$- to $C_{20}$-alkyl, $C_3$- to $C_8$-cycloalkyl, $C_5$- to $C_{20}$-aryl or alkylaryl, it being possible for these 4 radicals to be monosubstituted or disubstituted by halogen and $R^{10}$ is hydrogen or a poly-($C_2$- to $C_4$-alkylene oxide) radical whose terminal hydroxyl group can be etherified by an aliphatic $C_1$- to $C_{10}$-alkohol or esterified by a $C_1$- to $C_{10}$-carboxylic acid.

Among the radicals $R^5$ and $R^6$ in the formula II, the following groups are preferred:

unsubstituted alkyl radicals, in particular $C_1$- to $C_6$-alkyl radicals such as methyl, ethyl and propyl and also hydrogen. In addition, carboxymethyl groups or functional groups of the carboxymethyl groups are especially suitable.

Preferred radicals $R^5$, $R^6$ and $R^7$ which contain a functional derivative of a carboxyl group are those in which the carboxyl group is replaced by a group which can be hydrolyzed to a carboxyl group, ie., for example, by $C_1$- to $C_6$-alkoxycarbonyl or carbamoyl which may be mono- or disubstituted by $C_1$- to $C_6$-alkyl groups. Of course, the carboxyl group can also be present in neutralized form, ie. in salt form, for example in the form of an ammonium or alkali metal salt.

The functional derivatives of the carboxyl group also include the carbonyldioxy group by means of which 2 of the $R^5$, $R^6$ and $R^7$ can in each case be linked.

Particularly preferred $R^{4a}$ radicals are those in which $R^5$ is hydrogen and $R^6$ is carboxyl, carboxymethyl, methyl or likewise hydrogen.

The $R^7$ radical as defined preferably is or contains a carboxyl group. The carboxyl group can also be replaced by a functional derivative of the carboxyl group, preferred groups being the groups which are also suitable for the radicals $R^5$ and $R^6$. Very particularly preferred pyrazole derivatives are those which carry the following radicals:

$R^5$ -hydrogen $R^6$ -hydrogen, methyl, a carboxyl group, a carboxymethyl group or a functional derivative of the two last-mentioned groups $R^7$ —a carboxymethyl group, a 1-carboxyethyl group or functional derivatives of these groups.

The following combinations are preferred here:

$R^5$ hydrogen, $R^6$ carboxyl, $R^7$ carboxymethyl $R^5$ hydrogen, $R^6$ hydrogen, $R^7$ carboxymethyl $R^5$ hydrogen, $R^6$ hydrogen, $R^7$ 1-carboxyethyl The $R^{4b}$ radicals having the formula III mentioned under (b) preferably carry, as $R^8$ and $R^9$ substituents, hydrogen, methyl, ethyl or phenyl. In particular, both $R^8$ and $R^9$ are hydrogen or $R^8$ is hydrogen and $R^9$ is methyl.

Suitable $R^4$ radicals are in particular radicals having the formula IV

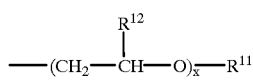   IV where $R^{11}$ is hydrogen, $C_1$- to $C_{20}$-alkyl, preferably $C_1$- to $C_6$-alkyl, $C_3$- to $C_8$-cycloalkyl, $C_1$- to $C_{20}$-acyl $R^{12}$ is hydrogen or methyl x is 1 to 10, preferably 2 to 6.

Suitable $R^{10}$ radicals are also those in which from 10 to 90 mol % of the alkylene glycol units are derived from propylene oxide and from 10 to 90 mol % of from ethylene oxide. These units can be either randomly distributed or bonded to the pyrazole derivative in the form of blocks.

Mixtures of pyrazole derivatives are particularly simply accessible which only differ with respect to the number of monomer units in the polyalkylene oxide radical.

Very particularly preferred pyrazole derivatives are the corresponding pyrazole derivatives of the formula Ib

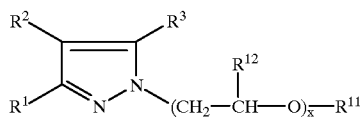   Ib

The pyrazole derivatives of the formula I, or Ia, which carry an $R^{4a}$ radical, can be prepared in a simple manner by reacting a pyrazole derivative of the formula V

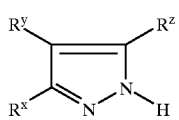   V where

I.

$R^x$ has the same meanings as $R^1$ $R^y$ has the same meanings as $R^2$ $R^z$ has the same meanings as $R^3$ or

II.

$R^x$ has the same meanings as $R^3$ $R^y$ has the same meanings as $R^2$ $R^z$ has the same meanings as $R^1$ or Va

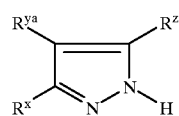   Va where $R^{ya}$ is halogen with a compound of the formula VI

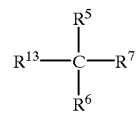   VI where the radical $R^{13}$ is chlorine or bromine.

The acid addition salts of the compounds of the formulae I, Ia and Ib are preferably those which are derived from mineral acids, eg. hydrochloric acid, sulfuric acid and phosphoric acid.

The reaction is conveniently carried out at from 0 to 150° C. under normal pressure in the absence of a solvent or in an inert solvent, eg. acetonitrile or dimethyl sulfoxide, in the presence of, based on the starting material of the formula III, approximately equimolar amounts of an alkali metal hydroxide such as sodium hydroxide and catalytic amounts of a phase-transfer catalyst. Suitable phase-transfer catalysts are $C_{10}$- to $C_{30}$-alkylammonium hydroxides, eg. octyltriethylammonium hydroxide.

According to another process, the pyrazole derivatives of the formula I or Ia which carry a radical $R^{4a}$ are obtained by reacting a pyrazole derivative of the formula V or Va in an addition reaction with a compound of the formula VII

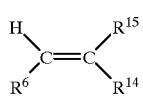   VII where the radical $R^6$ is hydrogen or a carboxyl group or a functional derivative of a carboxyl group, the radical $R^{14}$ is a carboxyl group or a functional derivative of a carboxyl group and the radical $R^{15}$ is hydrogen or methyl.

Suitable $R^{14}$ radicals are in particular those functional derivatives of the carboxyl group by which the carboxyl group in the $R^6$ radical can also be replaced.

The reaction can be carried out particularly simply using maleic anhydride, acrylic acid and methacrylic acid as well as the alkyl esters of the two acids mentioned.

For the reaction conditions pressure and temperature, what has been said for the reaction of compounds of the formula V with those of the formula VI applies.

Solvents which can be employed in addition to those which are suitable for the reaction of compounds of the formula V with those of the formula VI are also generally customary solvents, ie. alcohols, ethers, ketones, water and also alkanes.

The pyrazole derivatives I and Ib which carry an $R^{4b}$ radical can be prepared in a simple manner by reacting a pyrazole derivative of the formula V or Va with an appropriate epoxide of the formula VIII

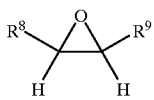

VIII which carries the desired radicals $R^8$ and $R^9$. This addition reaction is generally known and can be carried out by the generally known methods (cf. Methoden der Organischen Chemie [Methods of Organic Chemistry] (Houben-Weyl), 4th Edition, 1979, Volume VI/1a, Alcohols I, Part 1, pp. 373 to 380). Here the amount of the epoxide VII employed determines the size of X.

The preferred pyrazole derivatives, which contain several ethylene oxide and/or propylene oxide units, can be prepared particularly conveniently by one of the processes which is described in Methoden der Organischen Chemie [Methods of Organic Chemistry] (Houben-Weyl), 4th Edition, 1979, Volume XIV/2, Makromolekulare Stoffe [Macromolecular Substances], Part 2, pp. 425 to 460. In general, the reaction is carried out at from 40 to 200° C., preferably 80 to 140° C., under an excess pressure. The pressure is preferably that which establishes itself at the desired reaction temperature in a closed reaction vessel if the volume of the reaction vessel is selected such that the starting substances in liquid or solid form fill up at least 20, preferably at least 50%, of its volume.

The reaction proceeds under the conditions mentioned, but also without addition of a catalyst, it is recommended, however, to add catalytic amounts of water, alkali metal hydroxides such as sodium hydroxide or inorganic acids such as sulfuric acid or an activator such as alumina to the starting substances to accelerate the reaction.

When selecting a pyrazole derivative of the formula V or Va, it is to be taken into account that a radical $R^x$ in a pyrazole derivative of the formula V or Va corresponds in a pyrazole derivative of the formula I to a radical $R^1$, a radical $R^y$ to a radical $R^2$ and a radical $R^z$ to a radical $R^3$.

Since the pyrazole derivatives of the formula III tautomerize under the reaction conditions in which the reaction is customarily carried out

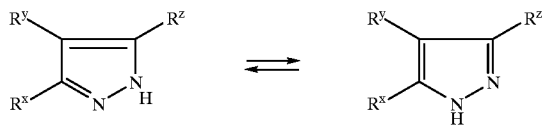

it cannot in general be avoided that, if the substituents $R^x$ and $R^y$ are different, isomer mixtures of the pyrazole derivatives of the formula I are formed which also contain a structural isomer in which a radical $R^z$ of the pyrazole derivative of the formula III corresponds to the radical $R^1$ and a radical $R^x$ corresponds to the radical $R^3$.

The acid addition salts of the compounds of the formulae I, Ia and Ib can be obtained by reacting these compounds with the corresponding acids, eg. by treating solutions of these compounds with stoichiometric amounts of acids and then removing the solvent.

The pyrazole derivatives can be marketed both in solid form and also in the form of their concentrated aqueous solutions.

The pyrazole derivatives of the formula I are used as nitrification inhibitors according to the generally customary processes: they can thus be applied, for example, directly to the soil in solid form as powder or granules.

It has also proven suitable to add mixtures of the nitrification inhibitor with a mineral fertilizer, in particular a nitrogen fertilizer. Such fertilizer mixtures preferably contain from 0.01 to 1% by weight of nitrification inhibitor, based on the mineral fertilizer.

The pyrazole derivatives having carboxyl groups or 2 to 6 ethylene oxide or propylene oxide units are particularly preferred, since they are highly water-soluble. The water solubility is therefore desirable since aqueous solutions of the nitrification inhibitors can be well metered on application to the soil and using them highly active long-term fertilizers can be prepared in a simple manner.

Fertilizer mixtures which contain from 20 to 1000% by weight, based on the fertilizer mixture, of water are particularly suitable. The amount of water is preferably selected here such that the fertilizer mixture is present as an aqueous solution.

Because of their good long-term action, fertilizer mixtures have proven particularly suitable which are prepared according to the following method:

Granules of mineral fertilizers such as, for example, ammonium-containing nitrates, sulfates or phosphates, are impregnated or coated with a nitrification inhibitor by spraying them with a solution of the nitrification inhibitor and drying again. The method is disclosed, for example, in DE-A 4 128 828, which is referred to here completely. The sealing of the impregnated granules with a paraffin wax also proposed there is in general unnecessary as a result of the significantly lower volatility of the nitrification inhibitors according to the invention.

The nitrification inhibitors are customarily applied to the soil in amounts from 100 g/ha to 10 kg/ha.

The pyrazole derivatives of the formula I which can be prepared in a simple manner from cost-effective starting materials are especially distinguished in their use as nitrification inhibitors in that they effectively inhibit the nitrification of ammonium nitrogen in the soil over a long period of time.

Added to this, these compounds are scarcely toxic, have a low vapor pressure and are well absorbed in the soil. This has the result that they are neither given off into the atmosphere by sublimation to a noticeable extent nor easily leached out by water. On the one hand this results in economic advantages such as a high economy on account of the longer-lasting action of the nitrification inhibitors and on the other hand in ecological advantages such as a decrease in the pollution of air and surface waters and ground water.

PREPARATION EXAMPLES

Example 1 (315932)

8.2 g of 3-methylpyrazole (0.1 mol) and 9.8 g of maleic anhydride (0.1 mol) were heated to 100° C. in 50 ml of 50% strength acetic acid. After 16 h the mixture was evaporated to dryness. On taking up the residue in diethyl ether the product (2-(N-3-methylpyrazolyl)succinic acid) precipitates in pure form and is filtered off: white crystals of m.p. 186° C. Yield 18.2 g (92%). 2 methyl signals (isomer distribution 2:1) are discernible in the NMR spectrum, which is in agreement with the abolition of the 3,5-tautomerism by the substitution on the nitrogen.

Example 2 (321300)

After neutralization with 4 g of NaOH, a solution of 10 g of 2-(N-3-methylpyrazolyl)succinic acid in 20 ml of water was treated with 65 ml of a 6% strength by weight NaOCl solution and 20 the mixture was reacted at room temperature for 12 h. The solution was then adjusted to a pH of from 2 to 4 using hydrochloric acid and the precipitate formed in this process was filtered off. The filtrate was acidified to pH 1, evaporated to dryness and taken up in MeOH. A precipitate which proves identical to the first can again be obtained from the methanolic solution by neutralization with triethylamine, (IR): white crystals of m.p.>250° C.; the NMR spectroscopic data and MS are in agreement with the structure of 2-(N-3-methyl-4-chloropyrazolyl)succinic acid.

Example 3 (315573)

6.8 g of pyrazole were initially introduced into 50 ml of acetonitrile and the mixture was treated with 5.6 g of KOH and 100 mg of octyltrimethylammonium hydroxide. Methyl chloroacetate is added dropwise at room temperature to this suspension. After 12 h at room temperature, the N-3-methylpyrazolylacetic ester had formed quantitatively.

After evaporating to dryness, the residue was taken up in ether and filtered. After distilling off the ether, the filtrate was subjected to a transesterification with formic acid, after which the volatile constituents having a boiling point up to 100° C. were distilled off at normal pressure. The residue was recrystallized from toluene. The pyrazolylacetic acid formed (yield 89%) had an m.p. of 172° C.

Example 4 (319782)

8.2 g of 3-methylpyrazole were processed as in Example 3. 12.7 g (91.5% of theory) of N-(3-methylpyrazolyl)acetic acid were obtained as white crystals of m.p. 143° C.

Example 5 (319225)

5.8 g (0.05 mol) of 4-chloro-3-methylpyrazole were processed as in Example 3. 7.6 g (87% of theory) of N-(3-methyl-4-chloropyrazolyl)acetic acid were obtained as a white powder of m.p. 155° C.

Example 6 (321233)

5.1 g of 4-chloropyrazole were processed as described in Example 3. 6.8 g of N-(4-chloropyrazolyl)acetic acid (m.p. 161 to 163° C.) were obtained.

Example 7 (176238)

6.8 g of pyrazole were reacted with ethyl 3-chloropropionate as in Example 3 and processed further in a similar manner. 11.8 g ([lacuna] of theory) of 3-(N-pyrazolyl)propionic acid are obtained as a white powder of m.p. 70° C.

Example 8 (319783)

8.2 g of 3-methylpyrazole were processed as in Example 7. 13.8 g of 3-(N-3-methylpyrazolyl)propionic acid are obtained as a white powder of m.p. 95° C.

Example 9 (319227)

5.8 g (0.05 mol) of 3-methyl-4-chloropyrazole were processed as in Example 7. 8.4 g of 3-(N-3-methyl-4-chloropyrazolyl)propionic acid are obtained as a white powder. By crystallization from ether, a modification of m.p. 103° C. is obtained, by crystallization from toluene a modification of m.p. 66 to 80° C.

Example 10 (321233)

50 g of methyl methacrylate (MMA) were dissolved in 82 g of 3-methylpyrazole and the mixture was stirred at 100° C. overnight. After fractionation under reduced pressure, the oily mixture of the 1,3- and 1,5-isomeric pyrazole derivatives, ie. of methyl 2-methyl-3-(N-3-methylpyrazolyl)propionate and of methyl 2-methyl-3-(N-5-methylpyrazolyl)propionate (boiling point 82° C. (0.01 mbar)) was obtained. Yield 90 g (99% based on MMA).

Example 10a 116.6 g (1.0 mol) of 4-chloro-3-methylpyrazole were heated to 100° C. and 137 g (1.07 mol) of n-butyl acrylate were added dropwise with stirring. After stirring overnight, the mixture of the isomeric esters [n-butyl 3-(N-4-chloro-3-methylpyrazolyl)propionate and n-butyl 3-(N-4-chloro-5-methylpyrazolyl)propionate] was fractionated in vacuo (boiling point: 116° C. (0.6 mbar)). Yield: 240 g (98%).

Example 10b 116.6 g (1.0 mol) of 4-chloro-3-methylpyrazole were reacted, as described in Example 10a, with 107.1 g (1.07 mol) of ethyl acrylate. Products were obtained which were similar to those of Example 10a.

Example 10c 96.2 g (1.0 mol) of 3,4-dimethylpyrazole were reacted as described in Example 10a. Products were obtained which were similar to those of Example 10a.

Example 11

4.4 g (0.1 mol) of ethylene oxide, which had been cooled to below the boiling point, were added dropwise in the course of about 3 h to a suspension of 100 ml of chloroform, 50 g of alumina (Merck alumina, activity grade 1, particle size 0.063–0.2 mm) and 8.2 g (0.1 mol) of 3-methylpyrazole. After a residence time of 12 h at room temperature, the alumina was filtered off and washed 3 times with a solution of 20 parts of methanol and 1 part of triethylamine. The filtrate and the wash solution were combined and the solvents were removed. 12.1 g of an oil remained, which consists to 95% by weight of 2-(N-methylpyrazolyl)ethanol (isomer distribution of the 1,3- and 1,5-pyrazole derivative positional isomers =2:1).

Example 12 (319899)

A 5 ml autoclave into which 2 g (0.025 mol) of 3-methylpyrazole and 0.1 ml of $H_2O$ had been initially introduced was filled with 2.2 g (0.05 mol) of ethylene oxide under an inert gas atmosphere and at −20° C. and sealed. The autoclave was then heated at 120° C. for about 12 h. Besides small amounts of unreacted 3-methylpyrazole, the material discharged from the reaction consisted of adducts of ethylene oxide to 3-methylpyrazole. These adducts are mixtures of pyrazolyl derivatives which are synthesized from a 3-methylpyrazolyl or 5-methylpyrazolyl unit and carry a hydroxyethyl group or a radical synthesized from several polyethylene oxide units. The main proportion are pyrazole derivatives having a radical consisting of 2 polyethylene oxide units (yield 60%).

Example 13 (319306)

5.8 g (0.1 mol) of propylene oxide were slowly added dropwise at 60° C. to a solution of 6.8 g (0.1 mol) of pyrazole, 0.1 ml of $HBF_4$ (40% strength aqueous solution) and 50 ml of water and the mixture was then reacted at this temperature for 3 h. The reaction mixture was worked up by fractional distillation under reduced pressure. 10 g of a fraction having a boiling point of 51° C. (0.02 mbar) were obtained. This was an isomer mixture of 85% of the monoadducts of pyrazole to the C atom of propylene oxide in the 1-position and 15% of the corresponding adduct in the 2-position.

Example 14 (310226)

11.6 g of 4-$C_1$-3-methylpyrazole (0.1 mol) were treated as in Example 13. Yield 14.2 g (82%). B.p. 75° C. (0.015 mbar). In the product mixture, in addition to the isomerism of the linkage of the heterocycle with PO described in Example 13, the 1,3- or 1,5-isomerism in the ring described in Example 11 is still observable by means of NMR. A total of four isomers were resolved in the gas chromatogram.

Example 15 (321234)

2 g (0.025 mol) of 4-methylpyrazole were reacted as described in Example 12. Products were obtained which were similar to those of Example 12.

Example 16 (321235)

2 g (0.025 mol) of 4-chloro-3-methylpyrazole were reacted as described in Example 12. Products were obtained which were similar to those of Example 12.

Example 17 (321236)

2 g (0.025 mol) of 4-chloropyrazole were reacted as described in Example 12. Products were obtained which were similar to those of Example 12.

Example 18

8.2 g (0.1 mol) of 3-methylpyrazole and 7.2 g of acrylic acid were refluxed for 16 h in 100 ml of tetrahydrofuran (THF). Quantitative conversion to 319783 (Ex. 8) could be monitored by GC. After stripping off the THF under reduced pressure, 14 g of pure substance (identical to Ex. 8) were obtained by recrystallization from toluene.

Example 18a 116.6 g (1.0 mol) of 4-chloro-3-methylpyrazole were heated to 100° C. and 77.1 g (1.07 mol) of acrylic acid were added dropwise with stirring. After stirring overnight, a viscous liquid was obtained which crystallized on standing. After recrystallization from acetone, 113 g (60%) of the mixture of the isomeric pyrazole derivatives 3-(N-4-chloro-3-methylpyrazolyl)propionic acid and 3-(N-4-chloro-5-methylpyrazolyl)propionic acid were obtained.

Example 18b 96.2 g (1.0 mol) of 3,4-dimethylpyrazole were reacted as described in Example 18a. Products were obtained which were similar to those of Example 18a.

Example 19

11.7 g of 4-chloro-3-methylpyrazole (0.1 mol) and 7.2 g of acrylic acid (0.1 mol) were treated as in Ex. 18. After cooling the reaction solution, 18 g of product (white powder) which spectroscopically (GC, NMR) proved identical to Example 9 (319227) were precipitated by addition of a two-fold excess (vol.) of pentene and 0° C.

B. Application tests

Volatility at room temperature

|  | Vapor pressure [mbar] |
|---|---|
| Examples | |
| Example 1 | $1.3 \times 10^{-13}$ |
| Example 4 | $1.1 \times 10^{-5}$ |
| Example 5 | $2.8 \times 10^{-7}$ |
| Example 8 | $1.3 \times 10^{-5}$ |
| Example 12 | $5.5 \times 10^{-4}$ |
| Comparison Examples | |
| 3-Methylpyrazole | $7.0 \times 10^{-2}$ |
| 4-chloro-3-methylpyrazole | $2.8 \times 10^{-3}$ |

The vapor pressure was measured at 20° C. according to OECD Guideline 79/831/EEC V, updated version of February 1990, Part A4.

We claim:

1. A method for nitrification inhibition, which comprises applying to a soil a pyrazole compound of the general formula I

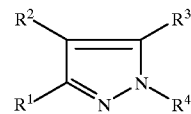

or an acid addition salt thereof, wherein the groups $R^1$, $R^2$, $R^3$ and $R^4$ have the following meanings:

$R^1$, $R^2$ and $R^3$ are halogen, nitro, hydrogen, $C_1$- to $C_{20}$-alkyl, $C_3$- to $C_8$-cycloalkyl, $C_5$-to $C_{20}$-aryl or alkylaryl, wherein the $C_1$- to $C_{20}$-alkyl, $C_3$- to $C_8$-cycloalkyl, $C_5$- to $C_{20}$-aryl or alkylaryl is, optionally, monosubstituted or disubstituted by halogen and/or hydroxy, $R^4$ is a (group $R^{4a}$ having the formula II

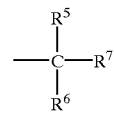

wherein $R^5$ and $R^6$ are hydrogen, $C_1$- to $C_{20}$-alkyl which is, optionally, monosubstituted or disubstituted by halogen and/or hydroxyl, a carboxyl group which may be neutralized to form a salt, a carboxymethyl group, a $C_1$- to $C_6$-alkoxycarbonyl group which may be mono- or di-substituted by $C_1$–$C_6$, alkyl groups, or a $C_1$ to $C_6$-carbamoyl group which may be mono- or di-substituted by $C_1$–$c_6$-alkyl groups, or $R^5$ and $R^6$ together form a carbonyldioxy (group and $R^7$ is a carboxyl group.

2. The method of claim 1, wherein the groups $R^1$, $R^2$, $R^3$ are $C_1$- to $C_5$-alkyl or halogen.

3. A pyrazole compound of the formula Ia

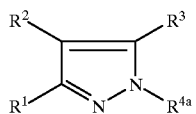

wherein $R^1$ and $R^3$ are nitro, hydrogen, $C_1$- to $C_{20}$-alkyl, $C_3$- to $C_8$-cycloalkyl, $C_5$- to $C_{20}$-aryl or alkylaryl, wherein the $C_1$- to $C_{20}$-alkyl, $C_3$- to $C_8$-cycloalkyl, $C_5$- to $C_{20}$-aryl or alkylaryl is, optionally, monosubstituted or disubstituted by halogen and/or hydroxy, $R^2$ is halogen, and $R^{4a}$ is a group having the formula II

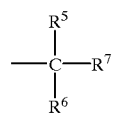

where $R^5$ and $R^6$ are hydrogen, $C_1$- to $C_{20}$-alkyl which is, optionally, monosubstituted or disubstituted by halo(en and/or hydroxyl, a carboxyl group which may be neutralized to form a salt, a carboxymethyl group, a $C_1$- to $C_6$-alkoxycarbonyl group which may be mono- or di-substituted by $C_1$–$C_6$-alkyl groups, or a $C_1$ to $C_6$-carbamoyl group which may be mono- or di-substituted by $C_1$–$C_6$-alkyl groups or $R^5$ and $R^6$ together form a carbonyldioxy group and $R^7$ is a carboxyl group, or an acid addition salt thereof.

4. The compound of claim 3, wherein $R^5$ is hydrogen; and $R^6$ is hydrogen or a carboxyl group or a substituent capable of being converted into a carboxyl group.

5. A process for preparing pyrazole compounds of claim 3, which comprises reacting a pyrazole compound of the formula Va

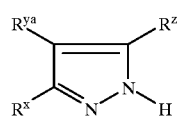

where $R^x$ and $R^z$ are halogen, nitro, hydrogen, $C_1$- to $C_{20}$-alkyl, $C_3$- to $C_8$-cycloalkyl, $C_5$- to $C_{20}$-aryl or alkylaryl, wherein $C_1$- to $C_{20}$-alkyl, $C_3$- to $C_8$-cycloalkyl, $C_5$- to $C_{20}$-aryl or alkylaryl is, optionally, monosubstituted or disubstituted by halogen and/or hydroxyl, and $R^{ya}$ is halogen with a compound of the formula VI

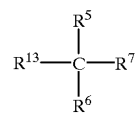

where $R^{13}$ is chlorine or bromine, those compounds being excluded where 2 of the groups $R^x$, $R^z$ or $R^{ya}$ are simultaneously halogen, wherein $R^5$, $R^6$, and $R^7$ are defined in claim 3.

6. A process for preparing compounds of claim 4, comprising reacting a pyrazole compound of the formula Va

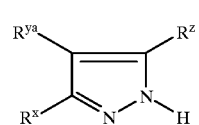

wherein $R^x$ and $R^z$ are halogen, nitro, hydrogen, $C_1$- to $C_{20}$-alkyl, $C_3$ to $C_8$-cycloalkyl, $C_5$- to $C_{20}$-aryl or alkylaryl, wherein the $C_1$- to $C_{20}$-alkyl, $C_3$- to $C_8$-cycloalkyl, $C_5$- to $C_{20}$-aryl or alkylaryl is, optionally, monosubstituted or disubstituted by halogen and/or hydroxyl, and $R^{ya}$ is halogen, wherein compounds in which 2 of the groups $R^x$, $R^z$ or $R^{ya}$ are simultaneously halogen are excluded, with a compound of the formula VII

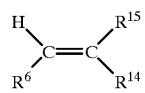

where $R^6$ is hydrogen, a carboxyl group or a substituent capable of being converted into a carboxyl group;

$R^{14}$ is a carboxyl group or a substituent capable of being converted into a carboxyl group and $R^{15}$ is hydrogen or methyl.

7. A fertilizer composition comprising:

(a) a mineral fertilizer, and (b) 100 to 10000 ppm by weight, based on the weight of the mineral fertilizer, of a pyrazole compound of formula I

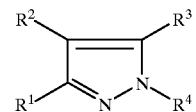

or an acid addition salt thereof, where the groups $R^1$, $R^2$, $R^3$ and $R^4$ have the following meanings:

$R^1$, $R^2$ and $R^3$ are halogen, nitro, hydrogen, $C_1$- to $C_{20}$-alkyl, $C_3$- to $C_8$-cycloalkyl, $C_5$-to $C_{20}$-aryl or alkylaryl, wherein the $C_1$- to $C_{20}$-alkyl, $C_3$- to $C_8$-cycloalkyl, $C_5$- to $C_{20}$-aryl or alkylaryl is, optionally, monosubstituted or disubstituted by halogen and/or hydroxy, $R^4$ is a group $R^{4a}$ having the formula II

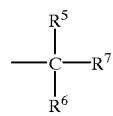

II wherein
$R^5$ and $R^6$ are hydrogen, $C_1$- to $C_{20}$-alkyl which is, optionally, monosubstituted or disubstituted by halogen and/or hydroxyl, a carboxyl group which may be neutralized to form a salt, a carboxymethyl group, a $C_1$- to $C_6$-alkoxycarbonyl (group which may be mono- or di-substituted by $C_1$-$C_6$ alkyl groups, or a $C_1$ to $C_6$-carbamoyl group may be mono- or di-substituted by $C_1$-$C_6$-alkyl groups,
or $R^5$ and R6 together form a carbonyldioxy group and $R^7$ is a carboxyl group.

8. A fertilizer comprising:

(a) a mineral fertilizer, and (b) 100 to 10000 ppm by weight, based on the weight of the mineral fertilizer, of pyrazole compound of claim 3.

9. A method of inhibiting nitrification, comprising applying to a soil an effective amount of the pyrazole compound of claim 3 to inhibit nitrification.

* * * * *